United States Patent
Wu et al.

(10) Patent No.: US 10,358,424 B2
(45) Date of Patent: *Jul. 23, 2019

(54) SODIUM SALT OF URIC ACID TRANSPORTER INHIBITOR AND CRYSTALLINE FORM THEREOF

(71) Applicant: Jiangsu Hengrui Medicine Co., Ltd., Lianyungang, Jiangsu (CN)

(72) Inventors: Guaili Wu, Jiangsu (CN); Zhenjun Qiu, Jiangsu (CN); Yunpeng Su, Jiangsu (CN); Xi Lu, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,696

(22) Filed: Oct. 11, 2018

(65) Prior Publication Data

US 2019/0040015 A1 Feb. 7, 2019

Related U.S. Application Data

(63) Continuation of application No. 15/574,328, filed as application No. PCT/CN2016/083423 on May 26, 2016, now Pat. No. 10,196,361.

(30) Foreign Application Priority Data

May 27, 2015 (CN) .......................... 2015 1 0280720

(51) Int. Cl.
| | | |
|---|---|---|
| C07D 215/36 | (2006.01) | |
| A61K 31/47 | (2006.01) | |
| A61P 3/00 | (2006.01) | |
| A61P 19/00 | (2006.01) | |

(52) U.S. Cl.
CPC ............ C07D 215/36 (2013.01); A61K 31/47 (2013.01); A61P 3/00 (2018.01); A61P 19/00 (2018.01); *C07B 2200/13* (2013.01)

(58) Field of Classification Search
CPC .............................. C07D 215/36; A61K 31/47
See application file for complete search history.

(56) References Cited

U.S. PATENT DOCUMENTS

| | | | |
|---|---|---|---|
| 9,637,484 B2* | 5/2017 | Peng | .................. C07C 323/62 |
| 2016/0108035 A1* | 4/2016 | Peng | .................. C07C 323/62 |
| | | | 514/262.1 |
| 2018/0134663 A1* | 5/2018 | Wu | .................. A61K 31/47 |

FOREIGN PATENT DOCUMENTS

| | | | |
|---|---|---|---|
| EP | 1820515 A1 | | 8/2007 |
| WO | 2014183555 | * | 11/2014 |
| WO | 2014183555 A1 | | 11/2014 |

OTHER PUBLICATIONS

Int'l Search Report dated Sep. 1, 2016 in Int'l Application No. PCT/CN2016/083423.
Written Opinion dated Sep. 1, 2016 in Int'l Application No. PCT/CN2016/083423.

\* cited by examiner

*Primary Examiner* — D Margaret M Seaman
(74) *Attorney, Agent, or Firm* — Panitch Schwarze Belisario & Nadel LLP

(57) ABSTRACT

Provided are a sodium salt of a uric acid transporter inhibitor and a crystalline form thereof, In particular, provided are a uric acid transporter (URAT1) inhibitor 1-((6-bromo-quinoline-4-yl)thio)cyclobutyl sodium formate (the compound of formula (I)), a crystal form I, and preparation method thereof. The obtained crystal form I of the compound of formula (I) has a good crystal form stability and chemical stability, and the crystallization solvent used has a low toxicity and low residue, and can be better used in clinical treatment.

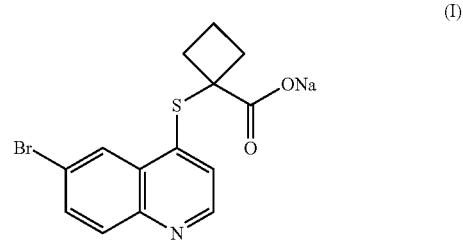

(I)

6 Claims, 2 Drawing Sheets

SODIUM SALT OF URIC ACID TRANSPORTER INHIBITOR AND CRYSTALLINE FORM THEREOF

CROSS-REFERENCE TO RELATED APPLICATION

This application is a Continuation of co-pending U.S. patent application Ser. No. 15/574,328, filed Nov. 15, 2017, which was a Section 371 of International Application No. PCT/CN2016/083423, filed May 26, 2016, which was published in the Chinese language on Dec. 1, 2016, under International Publication No. WO 2016/188444 A1, which claims priority under 35 U.S.C. § 119(b) to Chinese Application No. 201510280720.2, filed May 27, 2015, the disclosures of which are incorporated herein by reference in its/their entirety.

FIELD OF THE INVENTION

The present invention relates to sodium 1-((6-bromoquinolin-4-yl)thio)cyclobutane-1-carboxylate, a crystal form I thereof, and a preparation method and use thereof. The compound of formula (I) prepared according to the method of the present invention is useful in the treatment of gout disease.

BACKGROUND OF THE INVENTION

Recently, the prevalence of gout has increased each year, and the age of onset has shown a trend towards a younger age due to an improvement the standard of living.

Men and menopausal women are vulnerable to gout, and the peak incidence is 40-50 years old. The clinical features of gout are hyperuricemia, recurrence of gouty acute arthritis, deposition of gouty tophus, characteristic chronic arthritis and joint deformity. The kidney is generally involved, causing chronic interstitial nephritis and uratic nephrolithiasis. The prerequisite of gout is hyperuricemia, i.e. the saturated concentration of uric acid in serum at 37° C. is about 420 μmol/L (70 mg/L). One is suffering from hyperuricemia when the concentration of uric acid in serum is higher than the above-mentioned value. However, only some hyperuricemia patients develop gout, and its mechanism is unclear. Only hyperuricemia patients with deposition of urate crystal, arthritis and/or kidney disease, kidney stone etc. are considered to suffer from gout. Therefore, hyperuricemia is an important biochemical basis index of gout, and is closely related to the onset of gout. Hyperuricemia is closely related to the onset of hypertension, hyperlipidemia, atherosclerosis, obesity and insulin resistance, and has become a serious metabolic disease that threatens human health.

Uric acid is the final product of purine metabolism in humans. Uricase is absent due to genetic mutation of uricase during human evolution, and uric acid thus cannot be metabolized into soluble allantoin for removal from the body. Therefore, there is an excess of serum uric acid concentration in hyperuricemia patients. The onset of hyperuricemia is due to: (1) increased uric acid production, which accounts for 15% to 20% of gout onset, for example, diets enriched with purine are consumed in excess, or more uric acid is synthesized from amino acids and nucleotides in vivo, and excessive uric acid is produced from the catabolism of nucleic acids; and (2) decreased uric acid excretion and increased uric acid reabsorption, which are the main pathogenesis of hyperuricemia and gout, account for about 80% to 85% of gout onset. About 95% of uric acid reabsorption is performed by Uric Acid Transporter 1 (URAT1) located in the epithelial cells of the renal proximal tubule. URAT1 is a complete membrane protein located in the kidney, which belongs to the solute carrier 22 (SLC22) family. It performs urate-anion exchange, and is responsible for the regulation of uric acid levels in the blood. Therefore, URAT1 inhibitors could enhance the excretion of uric acid by inhibiting such reabsorption.

There are very few anti-gout drugs on the pharmaceutical market in China. Allopurinol and benzbromarone are still the main drugs, and no novel and better anti-gout drug has been developed. Febuxostat, approved by the FDA in 2009, is a xanthine oxidase (XO) inhibitor. It treats gout by reducing the production of uric acid. RDEA-594 (Lesinurad), developed by Ardea Biosciences Inc., enhances the excretion of uric acid by inhibiting Uric Acid Transporter 1 (URAT1), thereby achieving the purpose of reducing the serum concentration of uric acid. Its efficacy is not affected by renal function and the dosage of allopurinol. It does not alter the transport effect of Organic Anion Transporter 1/3 (OAT1/OAT3) within clinical dosage. In addition, it is more specific for its targets as compared with other uricosuric drugs, and has less interactions with other drugs.

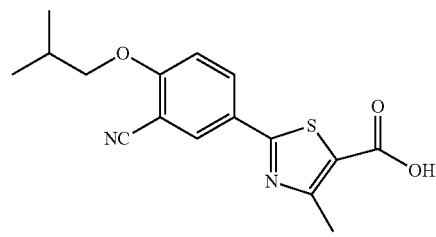

Febuxostat

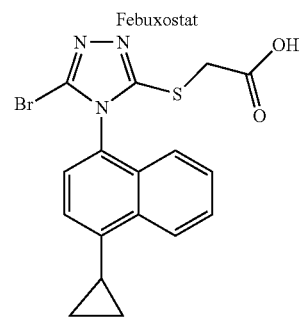

RDEA-594

The Structural Formulas of Febuxostat and RDEA-594

However, RDEA-594 was found in clinical trials of drugs for treating HIV infection, and its activity against uric acid transporter URAT1 is not high, with its 1050 being about 7 μM. Moreover, the dosage in clinical use is relatively high. Therefore, there is still much space to explore for the target uric acid transporter URAT1.

International Patent Application Publication WO2014183555 discloses a series of compounds with higher inhibitory activity of uric acid transporter URAT1. These compounds can effectively inhibit the reabsorption of uric acid and excrete uric acid from the body, thereby reducing the blood uric acid content continuously to achieve the purpose of treating gout. A compound as shown below is included:

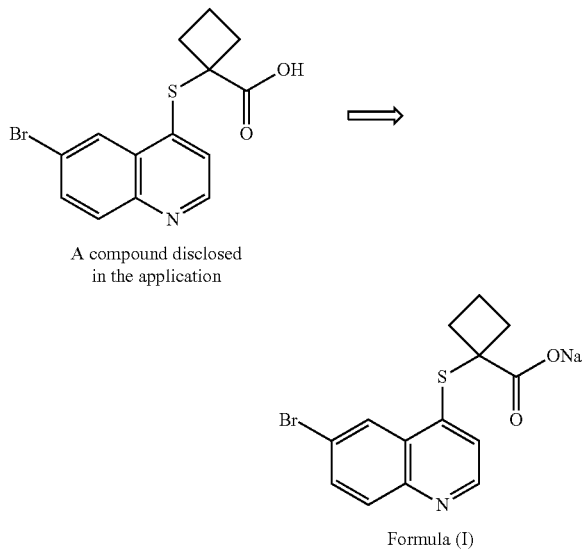

A compound disclosed in the application

Formula (I)

In order to further improve the solubility in water of this compound, the applicant has developed a sodium salt thereof (Formula I). The solubility in water has increased from almost insoluble to 0.14 mg/mL. On the other hand, the crystal structure of the pharmaceutically active ingredient often affects the chemical stability of the drug. Different crystallization conditions and storage conditions can lead to changes in the crystal structure of the compound, and sometimes the accompanying production of other crystal forms. In general, an amorphous drug product does not have a regular crystal structure, and often has other defects, such as poor product stability, smaller particle size, difficult filtration, easy agglomeration, and poor liquidity. Therefore, it is necessary to improve the various properties of the above-mentioned product. Based on the discovery of novel developing forms of the product, there is a need to identify a new crystal form with high purity and good chemical stability.

SUMMARY OF THE INVENTION

The object of the present invention is to provide a compound of formula (I), i.e. sodium 1-((6-bromoquinolin-4-yl)thio)cyclobutane-1-carboxylate. This compound, to a certain extent, improves the desired properties of the compound disclosed in WO2014183555, when used as a pharmaceutical active ingredient.

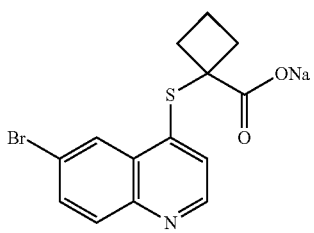

(I)

The compound of formula (I) can be obtained by reacting 1-((6-bromoquinolin-4-yl)thio)cyclobutane-1-carboxylic acid with sodium hydroxide.

The applicant has investigated a series of crystal products of the compound of formula (1) obtained under various crystallization conditions, and X-ray diffraction and differential scanning calorimetry (DSC) measurements have been conducted on the obtained crystal products. It was found that a stable crystal form, which is referred to as crystal form I, can be obtained under specific crystallization conditions. The DSC spectrum of crystal form I of the present application shows no absorption within 300° C., indicating that its melting point is greater than 300° C. The X-ray powder diffraction spectrum, which is obtained by using Cu-Ka radiation and represented by 2θ angle and interplanar distance (d value), is shown in FIG. 1, in which there are characteristic peaks at 9.08 (9.73), 11.73 (7.54), 12.19 (7.26), 15.59 (5.68), 16.28 (5.44), 17.73 (5.00), 18.16 (4.88), 18.80 (4.72), 19.48 (4.55), 20.80 (4.27), 23.16 (3.84), 27.54 (3.24) and 30.37 (2.94).

The present invention also provides a method of preparing crystal form I of the compound of formula (1). Specifically, the method comprises the following steps of:

(1) dissolving a solid sodium 1-((6-bromoquinolin-4-yl)thio)cyclobutane-1-carboxylate in any crystal form or amorphous form into an appropriate amount of solvent under heating, then cooling the solution to precipitate a crystal; and (2) filtering the crystal, then washing and drying it.

In step (1), the solvent is a mixed solvent of water and any of alcohols and ketones having 3 or less carbon atoms; more preferably water/isopropanol, water/acetone, acetone/water/acetone, or acetone/water/isopropanol.

In an embodiment of the present invention, the preferred mixed solvent is a mixed solvent of acetone/water/acetone, and the ratio is not particularly limited. In a preferred embodiment of the present invention, the volume ratio of the three is 1:1:5. When the mixed solvent is acetone/water/acetone, it means that sodium 1-((6-bromoquinolin-4-yl)thio)cyclobutane-1-carboxylate is dissolved in a mixed solvent of acetone/water until the solution is clear, then another part of acetone is added to precipitate a crystal. Acetone/water/isopropanol also refers to a similar meaning.

The recrystallization method is not particularly limited, and can be carried out by any conventional recrystallization process. For example, the material, i.e., the compound of formula (1), can be dissolved in an organic solvent under heating, and then the solution cooled slowly to precipitate a crystal under stirring. After the completion of crystallization, the desired crystal can be obtained via filtering and drying. In particular, the crystal obtained by filtration is usually dried in a vacuum under reduced pressure at a heating temperature of about 30 to 100° C., preferably 40 to 60° C., to remove the recrystallization solvent.

The resulting crystal form is determined by differential scanning calorimetry (DSC) and X-ray diffraction spectrum. Meanwhile, the residual solvent in the obtained crystal is also determined.

The crystal form of the compound of formula (I) prepared according to the method of the present invention does not contain or contains only a relatively low content of residual solvent, which meets the requirement of the National Pharmacopoeia concerning the limitation of the residual solvent of drug products. Therefore, the crystal of the present invention is suitable for use as a pharmaceutical active ingredient.

The research results show that crystal form I of the compound of formula (I) prepared according to the present invention is stable under conditions of lighting, high temperature and high humidity. Crystal form I is also stable under conditions of grinding, pressure and heating, which meets the production, transportation and storage requirements of drug products. The preparation process thereof is stable, repeatable and controllable, which is suitable for industrial production.

DETAILED DESCRIPTION OF THE INVENTION

The present invention is illustrated by the following examples in detail. The examples of the present invention are merely intended to describe the technical solution of the present invention, and should not be considered as limiting the scope of the present invention.

Test instruments used in the experiments

1. DSC spectrum

Instrument type: Mettler Toledo DSC 1 Stare$^e$ System

Purging gas: Nitrogen

Heating rate: 10.0° C./min

Temperature range: 40-300° C.

2. X-ray diffraction spectrum

Instrument type: Bruker D8 Focus X-ray powder diffractometer

Ray: monochromatic Cu-Kα ray (λ=1.5406)

Scanning mode: θ/2θ, Scanning range: 2-40°

Voltage: 40 KV, Electric current: 40 mA

Example 1

Figure 1:
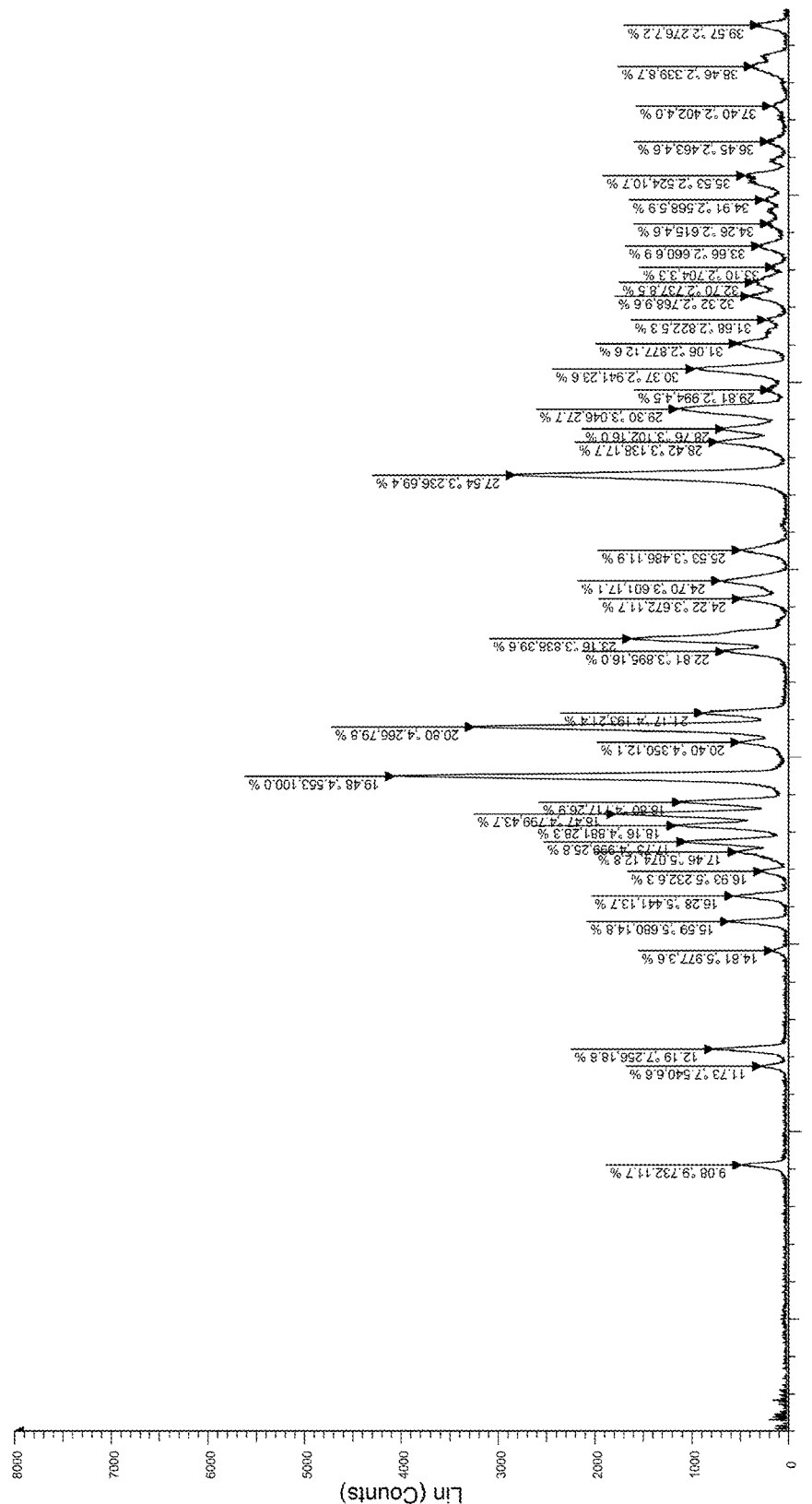
FIG. 1 shows the X-ray powder diffraction spectrum of crystal form I of the compound of formula (I)
Figure 2:
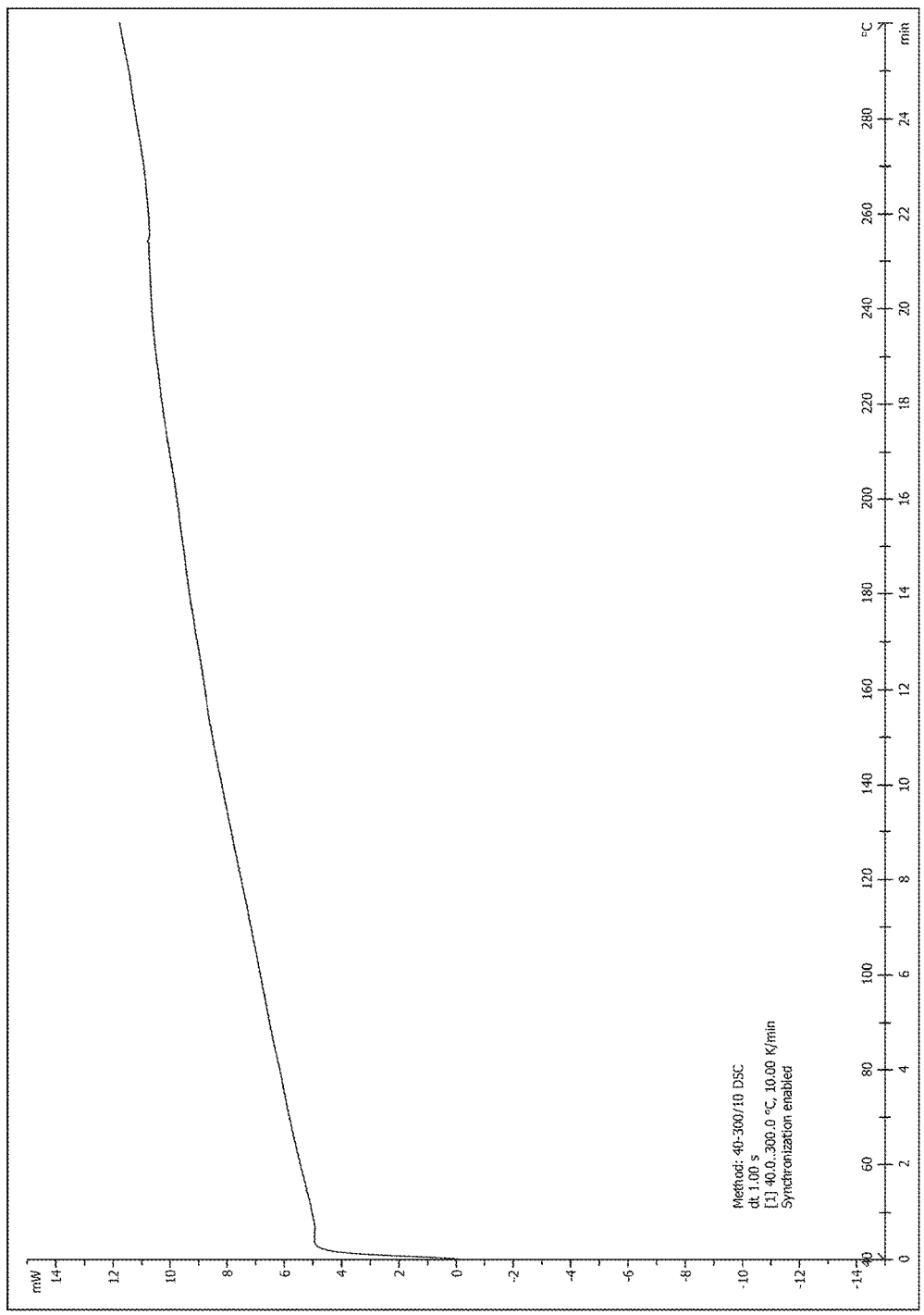
FIG. 2 shows the DSC spectrum of crystal form I of the compound of formula (1).

1-((6-Bromoquinolin-4-yl)thio)cyclobutane-1-carboxylic acid (prepared according to the method disclosed in WO 2014/183555) (1.0 g, 2.96 mmol) was added to a 50 mL three-necked reaction flask at 25° C., then 4.0 g of anhydrous ethanol were added. A 0.5 mL aqueous solution of sodium hydroxide (118 mg, 2.96 mmol) was added dropwise under stirring, then the reaction was stirred. The reaction was filtered, the filter cake was washed with anhydrous ethanol and dried in a vacuum at 40° C. Then, 850 mg of white to pale yellow powder was obtained in a yield of 84.0%. The X-ray powder diffraction spectrum of the crystal sample is shown in FIG. 1, in which there are characteristic peaks at about 9.08 (9.73), 11.73 (7.54), 12.19 (7.26), 15.59 (5.68), 16.28 (5.44), 17.73 (5.00), 18.16 (4.88), 18.80 (4.72), 19.48 (4.55), 20.80 (4.27), 23.16 (3.84), 27.54 (3.24) and 30.37 (2.94). The DSC spectrum is shown in FIG. 2, which shows no absorption within 300° C., indicating that its melting point is greater than 300° C. The crystal form was defined as crystal form I.

Example 2

The compound of formula (I) (prepared according to Example 1) (1.0 g, 2.78 mmol) was added to a 250 mL one-necked flask, then 30 mL of water were added. The mixture was heated to reflux until the solution was clear, then concentrated to about 3 mL under reduced pressure. Then, 150 mL of isopropanol were added slowly to precipitate a crystal under stirring. On the next day, the mixture was filtered and dried to obtain 689 mg of a white solid in a yield of 68.9%. The crystal sample was identified as crystal form I after studying and comparing the X-ray diffraction and DSC spectra.

Example 3

The compound of formula (I) (prepared according to Example 1) (1.0 g, 2.78 mmol) was added to a 150 mL one-necked flask, then 30 mL of water were added. The mixture was heated to reflux until the solution was clear, then concentrated to dryness under reduced pressure. Then, 30 mL of isopropanol were added directly to precipitate a crystal under stirring. On the next day, the mixture was filtered and dried to obtain 812 mg of a white solid in a yield of 81.2%. The crystal sample was identified as crystal form I after studying and comparing the X-ray diffraction and DSC spectra.

Example 4

The compound of formula (I) (prepared according to Example 1) (1.0 g, 2.78 mmol) was added to a 150 mL one-necked flask, then 30 mL of water were added. The mixture was heated to reflux until the solution was clear, then concentrated to about 3 mL under reduced pressure. Then, 30 mL of acetone were added slowly to precipitate a crystal under stirring. On the next day, the mixture was filtered and dried to obtain 918 mg of a white solid in a yield of 91.8%. The crystal sample was identified as crystal form I after studying and comparing the X-ray diffraction and DSC spectra.

Example 5

The compound of formula (I) (prepared according to Example 1) (1.0 g, 2.78 mmol) was added to a 150 mL one-necked flask, then 24 mL of acetone/water (v/v=1:1) were added. The mixture was heated to reflux until the solution was clear, then 60 mL of acetone were added slowly. The mixture was continuously refluxed for 10 minutes before the heating was stopped. Then, the mixture was stirred to precipitate a crystal. On the next day, the mixture was filtered and dried to obtain 688 mg of a white solid in a yield of 68.8%. The crystal sample was identified as crystal form I after studying and comparing the X-ray diffraction and DSC spectra.

Example 6

The compound of formula (I) (prepared according to Example 1) (1.0 g, 2.78 mmol) was added to a 150 mL one-necked flask, then 24 mL of acetone/water (v/v=1:1) were added. The mixture was heated to reflux until the solution was clear, then 60 mL of isopropanol were added slowly. The mixture was continuously refluxed for 10 minutes before the heating was stopped. Then, the mixture was stirred to precipitate a crystal. On the next day, the mixture was filtered and dried to obtain 752 mg of a white solid in a yield of 75.2%. The crystal sample was identified as crystal form after studying and comparing the X-ray diffraction and DSC spectra.

Example 7

The compound of formula (1) (prepared according to Example 1) (1.0 g, 2.78 mmol) was added to a 500 mL one-necked flask, then 30 mL of water were added. The mixture was heated to reflux until the solution was clear, then 300 mL of acetone were added slowly to precipitate a crystal under stirring. On the next day, the mixture was filtered and dried to obtain 728 mg of a white solid in a yield of 72.8%. The crystal sample was identified as crystal form I after studying and comparing the X-ray diffraction and DSC spectra.

Example 8

The sample of crystal form I prepared in Example 1 was spread flat in the air to test its stability under conditions of lighting (4500 Lux), heating (40° C., 60° C.), and high humidity (RH 75%, RH 90%). Samplings were carried out on Day 5 and Day 10. The purity as detected by HPLC is shown in Table 1.

TABLE 1

Stability of the sample of crystal form I of the compound of formula (I)

| Batch number | Time (day) | Lighting | 40° C. | 60° C. | RH 75% | RH 90% |
|---|---|---|---|---|---|---|
| S011303130715 | 0 | 99.76% | 99.76% | 99.76% | 99.76% | 99.76% |
|  | 5 | 99.75% | 99.73% | 99.73% | 99.74% | 99.74% |
|  | 10 | 99.70% | 99.73% | 99.71% | 99.74% | 99.73% |

The results of the stability study showed that the sample of crystal form I had good stability when it was spread flat in the air under conditions of lighting, high temperature and high humidity.

Example 9

Crystal form I of the compound of formula (I) prepared according to the method of Example 1 was ground, heated and pressed. The results showed that the crystal form is stable. The detailed experimental data are shown in Table 2 below.

TABLE 2

Special stability study of crystal form I of the compound of formula (I)

| Batch number | Treatment Process | Experimental procedure | Crystal form | DSC peak |
|---|---|---|---|---|
| S011303130715G | Grinding treatment for 10 minutes | 1 g of the sample of crystal form I of the compound of formula (I) was ground for 10 minutes in a mortar under nitrogen atmosphere. | Crystal form I | >300° C. |
| S011303130715H | Heating treatment for 3 hours at 80° C. | 1 g of the sample of crystal form I of the compound of formula (I) was spread flat and heated at 80° C. for 3 hours. | Crystal form I | >300° C. |
| S011303130715P | Pressing treatment | The sample of crystal form I of the compound of formula (I) was pressed to a slice. | Crystal form I | >300° C. |

Example 10

In the pharmacokinetic assay of the compound of Example 1 of the present invention, Sprague-Dawley (SD) rats were used as test animals. The compound of Example 1 was administrated intragastrically and intravenously to rats, then the drug concentration in the plasma at different time points was determined by a LC/MS/MS method to study the pharmacokinetic behavior and to evaluate the pharmacokinetic characteristics of the compound of the present invention in rats. The pharmacokinetic parameters of the compound of the present invention are shown in Table 3. The results showed that the compound of the present invention is well absorbed, and has a remarkable oral absorption effect. According to the mean value of AUC0-t, the absolute bioavailability of the compound after a single intragastric administration of 3 mg/kg in rats was calculated as 74.1%.

TABLE 3

Pharmacokinetic parameters of the compound after a single intragastric or intravenous administration in rats (n = 6, half male and half female)

| Mode of administration | Dosage (mg/kg) | Plasma concentration $C_{max}$ (µg/mL) | Area under curve $AUC_{0-t}$ (µg · h/mL) | Resistance time $MRT_{0-\infty}$(h) | Half life $t_{1/2}$ (h) |
|---|---|---|---|---|---|
| Intragastric adminis- | 3 | 10.5 ± 7.9 | 41.5 ± 27.2 | 6.15 ± 1.51 | 4.58 ± 0.85 |
|  | 9 | 22.0 ± 11.0 | 119 ± 65 | 7.11 ± 1.75 | 5.07 ± 2.08 |

TABLE 3-continued

Pharmacokinetic parameters of the compound after
a single intragastric or intravenous administration
in rats (n = 6, half male and half female)

| Mode of administration | Dosage (mg/kg) | Plasma concentration $C_{max}$ (μg/mL) | Area under curve $AUC_{0-t}$ (μg · h/mL) | Resistance time $MRT_{0-\infty}$ (h) | Half life $t_{1/2}$ (h) |
|---|---|---|---|---|---|
| tration | 27 | 38.8 ± 17.0 | 336 ± 241 | 7.09 ± 1.33 | 4.59 ± 0.50 |
| Intravenous administration | 3 | — | 56.0 ± 19.6 | 6.18 ± 1.33 | 5.50 ± 1.88 |

Example 11

In the pharmacokinetic assay of the compound of Example 1 of the present invention, Beagle dogs were used as test animals. The compound of Example 1 was administrated intragastrically and intravenously to dogs, then the drug concentration in the plasma at different time points was determined by a LC/MS/MS method to study the pharmacokinetic behavior and to evaluate the pharmacokinetic characteristics of the compound of the present invention in dogs. The pharmacokinetic parameters of the compound of the present invention are shown in Table 4. The results showed that the compound of the present invention is well absorbed, and has a remarkable oral absorption effect. According to the mean value of AUC0-t, the absolute bioavailability of the compound after a single intragastric administration of 3 mg/kg in dogs was calculated as 59.5%

TABLE 4

Pharmacokinetic parameters of the compound after a
single intragastric or intravenous administration in dogs
(n = 6, half male and half female)

| Mode of administration | Dosage (mg/kg) | Plasma concentration $C_{max}$ (μg/mL) | Area under curve $AUC_{0-t}$ (μg · h/mL) | Resistance time $MRT_{0-\infty}$ (h) | Half life $t_{1/2}$ (h) |
|---|---|---|---|---|---|
| Intragastric administration | 3 | 8.45 ± 2.1 | 8.63 ± 3.44 | 3.03 ± 1.03 | 3.49 ± 1.20 |
|  | 9 | 27.6 ± 4.8 | 37.5 ± 10.8 | 3.48 ± 1.36 | 3.83 ± 2.00 |
|  | 27 | 78.6 ± 22.0 | 105 ± 30.9 | 3.38 ± 0.96 | 4.31 ± 1.60 |

TABLE 4-continued

Pharmacokinetic parameters of the compound after a
single intragastric or intravenous administration in dogs
(n = 6, half male and half female)

| Mode of administration | Dosage (mg/kg) | Plasma concentration $C_{max}$ (μg/mL) | Area under curve $AUC_{0-t}$ (μg · h/mL) | Resistance time $MRT_{0-\infty}$ (h) | Half life $t_{1/2}$ (h) |
|---|---|---|---|---|---|
| Intravenous administration | 3 | — | 14.5 ± 3.6 | 3.57 ± 1.89 | 4.51 ± 2.25 |

What is claimed is:

1. An isolated sodium 1-((6-bromoquinolin-4-yl)thio)cyclobutane-1-carboxylate of formula (I):

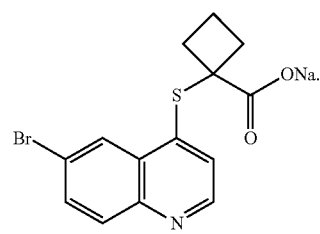

(I)

2. A method of preparing the isolated sodium 1-((6-bromoquinolin-4-yl)thio)cyclobutane-1-carboxylate of formula (I) according to claim 1, comprising reacting 1-((6-bromoquinolin-4-yl)thio)cyclobutane-1-carboxylic acid with sodium hydroxide.

3. A pharmaceutical composition comprising the isolated sodium 1-((6-bromoquinolin-4-yl)thio)cyclobutane-1-carboxylate of formula (I) according to claim 1, and a pharmaceutically acceptable carrier.

4. A method of inhibiting Uric Acid Transporter (URAT1) in a subject in need thereof, the method comprising administering to the subject the pharmaceutical composition according to claim 3.

5. The method according to claim 4, wherein the subject is in need of the treatment of gout.

6. A method of treating gout in a subject in need thereof, the method comprising administering to the subject the pharmaceutical composition of claim 3.

* * * * *